United States Patent [19]

Ligorati et al.

[11] 4,169,211
[45] Sep. 25, 1979

[54] PROCESS FOR THE PRODUCTION OF 2,2-(4,4'-DIHYDROXYDIPHENYL)PROPANE

[75] Inventors: Ferdinando Ligorati; Vittorio E. Nova; Giancarlo Aglietti, all of Milan, Italy

[73] Assignee: Società' Italiana Resine S.I.R. S.p.A., Milan, Italy

[21] Appl. No.: 815,406

[22] Filed: Jul. 13, 1977

Related U.S. Application Data

[63] Continuation of Ser. No. 419,835, Nov. 28, 1973, abandoned.

[30] Foreign Application Priority Data

Nov. 30, 1972 [IT] Italy ............................. 32276 A/72

[51] Int. Cl.$^2$ ................... C07C 37/22; C07C 37/38
[52] U.S. Cl. ........................................ 568/724; 568/728
[58] Field of Search ................ 260/619 A; 568/724, 568/728

[56] References Cited

U.S. PATENT DOCUMENTS

| 2,191,831 | 2/1940 | Perkins | 260/619 A |
| 2,959,622 | 11/1960 | Grimme et al. | 260/619 A |
| 3,073,868 | 1/1963 | Prahl et al. | 260/619 A |
| 3,111,544 | 11/1963 | Jous et al. | 260/619 A |
| 3,192,270 | 6/1965 | Meyer et al. | 260/619 A |

OTHER PUBLICATIONS

Kirk-Othmer, "Ency. of Science and Tech", (I) vol. 1, pp. 459-460, (II), vol. 4, pp. 149-158 (1963).

*Primary Examiner*—Norman Morgenstern
*Attorney, Agent, or Firm*—Sughrue, Rothwell, Mion, Zinn and Macpeak

[57] ABSTRACT

Process for the production of 2,2-(4,4'-dihydroxydiphenyl) propane comprising reacting phenol with acetone in a molar ratio of at least 2:1 but not exceeding 10:1 in the presence of an acidic agent at a temperature not exceeding 80° C. to substantially complete reaction of the acetone, separating the acidic agent from the reaction product, bringing the product freed from acidic agent into contact with a material chosen from between activated carbon and active earths at a temperature in the range of from about 60° to 120° C. for a time in the range of from about 1 to 120 minutes and distilling the product obtained in the treatment with the active material to recover the 2,2-(4,4'-dihydroxydiphenyl-propane.

9 Claims, No Drawings

PROCESS FOR THE PRODUCTION OF 2,2-(4,4'-DIHYDROXYDIPHENYL)PROPANE

This is a continuation of application Ser. No. 419,835, filed Nov. 28, 1973, now abandoned.

The present invention relates of an improved process for the production of 2,2-(4,4'-dihydroxydiphenyl)propane, and more particularly of 2,2-(4,4'-dihydroxydiphenyl)propane having a high purity.

DESCRIPTION OF THE PRIOR ART 2,2-(4,4'-Dihydroxydiphenyl)propane, which is commonly known as "bisphenol A", a name that will always be used from now on in the shorter form "bisphenol" for simplicity, is the product of the condensation of 2 molecules of phenol with 1 molecule of acetone. The condensation described is catalysed by acidic substances.

In practice, bisphenol is prepared by reaction of acetone with an excess of phenol in the presence of strong acids and possibly also accelerators.

Sulphuric acid and above all hydrochloric acid are normally used as strong acids, while mercaptans or mercapto acids are used as accelerators.

The reaction yields a crude mixture containing numerous undesirable by-products in addition to bisphenol, unreacted phenol and acetone, strong acid, activator if present, and water from the reaction.

These undesirable by-products include, for example, isomers of bisphenol having properties very different from those of the latter, particularly 2,2-(2,4'-dihydroxydiphenyl)propane and 2,2-(2,2'-dihydroxydiphenyl)propane, complex products such as the so-called "codimer" (2,2,4-trimethyl-4-p-hydroxyphenylchroman), condensation products such as trisphenol, higher condensation products in the form of tar-like high-boiling substances, and decomposition products.

The presence of the by-products described presents considerable disadvantages, both because of the tendency of such products to remain in the final product and because of the tendency to confer undesirable colours on the final product.

These tendencies are very often so pronounced that the use of the final product is impaired and this is not confined to cases where high purity is required.

Moreover, the presence of decomposition products inhibits some reactions in which bisphenol can be used, such as the preparation of polycarbonates.

The importance of obtaining bisphenol of high purity thus seems clear, and numerous methods for this purpose have been proposed in the art.

In one of these methods (see U.S. Pat. No. 2,191,831) the crude reaction mixture is treated in such a way as to separate the bisphenol directly in the crystalline form.

The disadvantage of this method is its considerable complication and hence its expensiveness, not only because of the need for numerous washes to which the crystalline bisphenol obtained must be subjected, but also because the unwanted by-products accumulate in the mother liquor from the crystallization and present the problem of their removal from the latter.

Only in this way is it possible to recycle the mother liquor to the condensation zone and to recover the desired components that are present in the liquid.

Moreover, the method described is also disadvantageous because the yield of bisphenol is not very high.

In another method (see Italian Pat. No. 650 774) the bisphenol is separated by crystallization of its addition product with phenol. In this case, part of the desired products remains in the mother liquor of the condensation process and part in the recrystallization mother liquor, and recovery operations must therefore be carried out on both phases. This makes such a process complicated and particularly costly.

In yet another method (see French Pat. No. 1,374,477) the crude condensation mixture is subjected to fractional distillation to separate initially the unreacted compounds and then the bisphenol, which is purified by extraction or recrystallization. Considerable losses occur in this case. To obtain a very pure bisphenol, moreover, the extraction or the recrystallization must generally be repeated many times.

Despite the observation of numerous precautions in the distillation, this method is characterized by decomposition of the bisphenol, which leads to the presence of new undesirable impurities in the bisphenol, particularly products that give unsatisfactory colour characteristics.

Finally, the fact that some components, particularly the isomers of bisphenol, have boiling points very close to that of bisphenol often makes a complete separation by distillation rather difficult and not very effective in practice.

SUMMARY

The object of the present invention is to provide a simple and economical process for the production of bisphenol having a very high purity.

It has been found that the disadvantages described above can be avoided and the desired object can be achieved by the process of the present invention.

This process consists essentially in reacting an excess of phenol with acetone in the presence of an acidic agent at a temperature not higher than 80° C. to substantially complete reaction of the acetone, separating the acidic agent from the reaction product, bringing the product freed from the acidic agent into contact, under the conditions described below, with a material selected from the group consisting of activated carbon and active earths, and distilling the product obtained in order to recover the bisphenol.

More precisely, according to the process of the application, the phenol is mixed with the acetone in a molar ratio of at least 2:1 and not exceeding 10:1.

The mixture is then brought to a temperature of from about 40° to 80° C. and an acidic agent, preferably hydrochloric acid and more preferably anhydrous hydrogen chloride, is added.

The pressure may be varied within the range from about 1 to 20 atm by regulation of the feed of hydrochloric acid, which is introduced in the gaseous form.

The mixture is maintained under the conditions indicated for a time of from about 1 to 10 hours sufficient to cause the substantially complete reaction of the acetone.

The reaction may be carried out continuously or discontinuously in one or more reactors.

It is also possible to carry out the reaction in the presence of small quantities, in any case not exceeding about 5% by weight of the bisphenol finally formed, of an aromatic or paraffinic, chlorinated or unchlorinated organic solvent whose boiling points is not higher than about 150° C.

The separation of the acidic agent, i.e. the hydrogen chloride, from the reaction product may be carried out by the means normally known for this purpose.

For example, an inert gas may be blown in or the product may be introduced into a chamber maintained at a pressure below atmospheric pressure.

The degassed product is then brought into contact, at a temperature of from about 60° to 120° C., for a time of from about 1 to 120 minutes, with a material selected from the group consisting of activated carbon and active earths.

These latter are materials that are widely known and described, for example in Kirk-Othmer: Encyclopedia of Chemical Technology, 1st Ed., Vol. 2, pp. 881-898 and Vol. 4, pp. 53-56.

The materials, which may be in any divided form, for example as spherical granules, cylindrical pellets, irregular granules, and the like, should have dimensions of from about 1 to 5 mm, porosities of from about 0.1 to 0.9 cc/g, and pores with radii of from about 10 to 1000 Å.

In a preferred embodiment of the invention, activated carbon, for example that obtained from bituminous coals, is used.

The degassed product may be brought into contact with the activated material by a means already known in the art for bringing an activated material and a liquid into contact. For example, the activated material and the degassed liquid product are mixed, the whole is left in contact for the times and at the temperatures indicated above, and the liquid is finally separated from the solid by filtration or centrifugation.

In the preferred embodiment of the invention, the contact is brought about by allowing the degassed product to percolate through a fixed bed of activated carbon, the percolation rate being adjusted so that the contact time is in the preferred range of from about 20 to 60 minutes.

To facilitate the percolation and to bring the temperature to values closer to the lower limit indicated, small additions of an organic solvent may be made to the product to be percolated, particularly a light aromatic solvent having a boiling point below 136° C., such as benzene, toluene, or ethylbenzene, or a light paraffinic solvent having a boiling point below 126° such as linear or branched hexanes, heptanes and octanes or their mixtures. The addition must in any case be adjusted in such a way that the quantity of solvent added is not greater than 10% with respect to the weight of the bisphenol present in the degassed product.

Finally, the product obtained from the treatment by contact with the activated material is subjected to a distillation to separate the phenol and any other compounds having boiling points close to that of phenol.

The distillation is carried out at a pressure below atmospheric pressure, preferably by the thin-film technique.

In every case, the pressure is maintained at values of from about 1 to 20 mm Hg, with distillation temperatures of from about 160° to 200° C.

In this way, a bisphenol having a Hazen colour not exceeding 25 and a crystallization point equal to or higher than 156.5° C. is obtained from the distillation.

In the description and in the examples, the purity of the bisphenol produced is always expressed and defined on the basis of the colour and the crystallization point. The latter is determined in the usual manner by melting the bisphenol at 160° C. and causing it to crystallize by the appropriate means. The colour, on the other hand, is determined by the Hazen method (ASTM D 1209), which consists in dissolving the bisphenol in methanol to give a solution containing 50% by weight and comparing the colour of this solution with that of standardized solutions.

The bisphenol produced in this way can be used directly in the majority of cases, for example in the preparation of epoxy resins. If a bisphenol of still higher purity is desired, such as is required for some applications, e.g. for the production of polycarbonates, it is preferable to recrystallize the bisphenol from the distillation described above from a solvent.

Solvents of the aromatic type, such as benzene and toluene, or of the paraffinic type, such as hexane, heptane, or various mixtures of paraffins, may be used for this purpose. Other solvents that can be used consist of halogenated, or better, chlorinated paraffins such as chloromethane, trichoroethylene, and the like.

In the crystallization, moreover, weight ratios of bisphenol to solvent of from about 0.1:1 to 1:1 are used, depending on the type of solvent used and the solubility of bisphenol in it.

The temperatures that may be used for this purpose are of the order of 100° C.

The operation is therefore carried out under pressure when low-boiling solvents are used or at normal pressure with solvents having higher boiling points.

In this way, the recrystallization yields a bisphenol having a Hazen colour not exceeding 10 and a crystallization point equal to or higher than 157° C.

Important advantages are also achieved when the phenol and any other products having boiling points close to that of phenol that are separated in the distillation described above, in practice the distillate, are recycled to the stage of the condensation reaction.

In particular in this case there is a decrease in the formation of the by-products formed and the possibility of using milder reaction conditions.

In any case, one of the essential points for the purposes of the invention is that the stages of the process are carried out in the order described above.

Thus it has been found that when the order of the treatment with activated material and the distillation under reduced pressure is changed, i.e. in practice when the treatment with activated material is carried out not on the crude degassed product but on the bisphenol from the distillation, products of the desired purity are not obtained.

It has also been found that even when, with the order of the treatment and the distillation still changed, the bisphenol obtained by distillation is subjected to treatment with activated material, dissolved in an organic solvent, and then crystallized from the latter after the treatment, one does not obtain results comparable to those obtained by the process of the invention.

The invention will now be further illustrated by the following examples, which are not intended to limit it in any way.

Examples 3 and 5 are comparison examples.

When values are given in percentages, they are intended to be taken as percentages by weight unless otherwise indicated.

The invention is further illustrated by the following non-limiting examples.

EXAMPLE 1

940 g of phenol and 58 g of acetone were introduced into an autoclave at a temperature of 50° C., and anhydrous hydrogen chloride was added until a pressure of 10 kg/cm$^2$ was reached in the reaction space.

After the temperature of the mixture had been brought to 60° C. and maintained at this value for 4 hours, the introduction into the autoclave of a mixture of phenol and acetone identical with that initially charged was started.

With a feed rate of 250 g/hour of the mixture described above, an equivalent quantity of reacted mixture was simultaneously removed.

The reacted mixture was then introduced into a degassing tower consisting of a heat resistent glass tube (Pyrex) having a diameter of 2.5 cm and a height of 50 cm, packed with 5×5 mm Raschig rings and maintained at 80° C. and at a pressure of 1 atmosphere absolute, where the hydrogen chloride dissolved in the mixture was separated. The degassed mixture was passed at a temperature of 100° C. over a fixed bed of activated carbon obtained from bituminous coals in the form of granules having dimensions of from 3 to 5 mm, a porosity of 0.9 cc/g, and pores having a radius of 10 to 500 Å. The rate of percolation of degassed mixture in the fixed bed was adjusted so that the residence time was about 20 minutes.

This led to a clear, limpid product, which was transferred to a thin-film evaporator of the Luwa type operating at a temperature of 160° C. and a pressure of 10 mm Hg.

The phenol and the other compounds having boiling points close to that of phenol were thus separated at the top, and a bisphenol having the following characteristics at the bottom:

Hazen colour (50% in methanol)—25
Crystallization point—156.6° C.
Isomers—0.25%
Co-dimer—0.08%
Trisphenol—0.05%
Phenol—0.01%

These last concentrations, as in the following examples, were determined by gas-chromatographic analysis.

EXAMPLE 2

The bisphenol separated at the base of the thin-layer evaporator of the Luwa type of Example 1 was recrystallized from toluene.

For this purpose it was dissolved in toluene at a temperature of 112° C. at atmospheric pressure in a proportion of 0.2 parts by weight per part by weight of toluene.

The resulting solution was then cooled to 40° C. to bring about the recrystallization of the bisphenol present, which was separated by filtration.

After drying in a vacuum oven at 105° C. for a time of 1 hour, a product was obtained that was practically free from impurities and had the following characteristics:

Hazen colour (50% in methanol)—10
Crystallization point—157.0° C.
Isomers—0.02%
Co-dimer—absent
Trisphenol—absent
Phenol—0.005%

This product was particularly suitable for the preparation of polycarbonates.

EXAMPLE 3 (comparison)

The mixture from the autoclave of Example 1, again degassed as in Example 1, was transferred at once to a thin-film evaporator of the Luwa type operating at a temperature of 160° C. and at a pressure of 10 mm Hg.

The phenol and all the other low-boiling compounds were thus separated at the top, and a bisphenol having a Hazen colour (50% in methanol) of 400 and a crystallization point of 154.2° C. at the bottom.

This product, after liquefaction at a temperature of 160° C., was allowed to percolate through a fixed ben of activated carbon was in Example 1.

The rate of percolation of the liquid bisphenol was adjusted so that the residence time was about 120 minutes.

A bisphenol having the following characteristics was obtained:

Hazen colour (50% is methanol)—100
Crystallization point—156.4
Isomers—0.30%
Co-dimer—0.07%
Trisphenol—0.05%
Phenol—0.01%

EXAMPLE 4 n-Hexane was added at a rate of 5 g/hour to the mixture (250 g/hour) from the autoclave of Example 1, again degassed as in Example 1.

The mixture obtained was allowed to percolate at a temperature of 60° C. through a fixed bed of activated carbon as in Example 1.

The rate of percolation of the mixture was adjusted so that the residence time was about 60 minutes. The product obtained was transferred to a thin-film evaporator of the Luwa type operating at a temperature of 160° C. and at a pressure of 10 mm Hg.

The phenol and the other low-boiling compounds were thus separated at the top, while a bisphenol having the following characteristics was separated at the bottom:

Hazen colour (50% in methanol)—15
Crystallization point—156.8° C.
Isomers—0.2%
Co-dimer—0.05%
Trisphenol—absent
Phenol—0.01%

EXAMPLE 5 (comparison)

500 g of bisphenol obtained at the base of the thin-film evaporator of the Luwa type of comparison example 1 (Hazen colour 400 and crystallization point 154.2° C.) were dissolved in 500 g of benzene at a temperature of 100° C.

The solution obtained was passed into a column packed with activated carbon of the type of Example 3, the temperature being maintained at 100° C. with a pressure of 5 atm.

The rate of percolation of the solution was adjusted so that the residence time was about 120 minutes.

The percolated solution was then brought to room temperature in order to crystallize the bisphenol present, which was separated by filtration.

After drying in a vaccum oven at 100° C. for a time of 1 hour, a product having the following characteristics was obtained:

Hazen colour (50% in methanol)—50
crystallization point—156.3
Isomers—0.02%
Co-dimer—0.05%
Trisphenol—0.05%
Phenol—0.01%

EXAMPLE 6

470 g of phenol and 58 g of acetone were introduced into an autoclave at 40° C. and anhydrous hydrogen chloride was introduces until the pressure reached 5 kg/cm².

After reaction for 4 hours, a mixture consisting of:
- 200 g of fresh phenol,
- 23 g of toluene
- 293 of the recycled mixture of phenol and other compounds having boiling points close to that of phenol obtained as the distillate in the thin-film evaporator was fed into the autoclave, the same temperature still being maintained, and 516 g/hour of reacted mixture was simultaneously removed.

The latter was then passed into a degassing tower as in Example 1, maintained at a pressure of 1 atmosphere absolute, where the hydrogen chloride dissolved in the mixture was separated.

The degassed mixture was passed at a temperature of 60° C. through a fixed bed of activated carbon as in Example 1.

The rate of percolation of the degassed mixture in the fixed bed was adjusted so that the residence time was about 10 minutes.

The product obtained was then transferred to a thin-film evaporator of the Luwa type at a temperature of 180° C. and a pressure of 10 mm Hg.

The phenol and the other products having boiling points close to that of phenol were thus separated at the top, and were recycled to the autoclave, while a bisphenol having the following characteristics was separated at the base:

- Hazen colour (50% in methanol)—20
- Crystallization point—156.8° C.
- Isomers—0.2%
- Co-dimer—0.1%
- Trisphenol—0.05%
- Phenol—0.01%.

What we claim is:

1. In a process for the production of 2,2-(4,4'-dihydroxydiphenyl)-propane characterized by hazen color not exceeding 25 and a crystallization point of at least 156.5° C. comprising the steps of:
   (a) reacting phenol with acetone in a molar ratio of at least 2:1 but not exceeding 10:1 in the presence of an acidic agent at a temperature not exceeding 80° C. to substantially complete reaction of the acetone,
   (b) separating the acidic agent from the reaction product, and
   (c) distilling the product at a pressure of from about 1 to 20 mm Hg and at a distillation temperature of from about 160° to 200° C. to recover the 2,2-(4,4'-dihydroxydiphenyl)-propane, wherein the improvement comprises bringing the product from step (b) freed from acidic agent into contact with a material selected from the group consisting of activated carbon and active earths at a temperature of from about 60° to 120° C. for a time of from about 10 to 120 minutes prior to carrying out said distillation step (c), whereby said 2,2-(4,4'-dihydroxydiphenyl)-propane having a hazen color not exceeding 25 and a crystallization point of at least 156.5° C. is produced.

2. The process of claim 1, wherein the reaction of phenol with acetone is carried out at a temperature of from about 40° to 80° C. and at a pressure of from about 1 to 20 atmospheres for a time of from about 1 to 10 hours.

3. The process of claim 1, wherein hydrochloric acid is used as the acidic agent.

4. The process of claim 1, wherein the reaction of phenol with acetone is carried out in the presence of a solvent in a quantity not exceeding 5% with respect to the weight of the 2,2-(4,4'-dihydroxydiphenyl)propane finally formed, the said solvent being selected from the group consisting of aromatic and paraffinic, chlorinated or unchlorinated hydrocarbons having a boiling point below 150° C.

5. The process of claim 1, wherein the active material is present in a divided form, with dimensions of from about 1 to 5 mm, a porosity of from about 0.1 to 0.9 cc/g, and pores having a radius of from about 10 to 1000 Å.

6. The process of claim 1, wherein activated carbon obtained from bituminous coals is used as the active material.

7. The process of claim 1, wherein the contact of the deacidified condensation product with the active material is brought about by allowing the deacidified product to percolate through a fixed bed of activated carbon, the percolation rate being adjusted so that the contact time is in the range of from about 10 to 120 minutes.

8. The process of claim 1, wherein an aromatic organic solvent having a boiling point below 136° C. or a paraffinic organic solvent having a boiling point below 126° C. is added to the deacidified condensation product in a quantity not exceeding 10% with respect to the weight of the 2,2-(4,4'-dihydroxydiphenyl)-propane present in the condensation product itself.

9. The process of claim 1, wherein the distillation of the product obtained in the treatment with the active material is carried out by the thin-film technique.

* * * * *